(12) United States Patent
Li

(10) Patent No.: US 8,706,192 B2
(45) Date of Patent: Apr. 22, 2014

(54) MAGNETIC RESONANCE ELASTOGRAPH SYSTEM WITH HYDRAULIC DRIVER

(76) Inventor: Geng Li, Hong Kong (HK)

( * ) Notice: Subject to any disclaimer, the term of this patent is extended or adjusted under 35 U.S.C. 154(b) by 945 days.

(21) Appl. No.: 12/370,583

(22) Filed: Feb. 12, 2009

(65) Prior Publication Data

US 2009/0209847 A1 Aug. 20, 2009

Related U.S. Application Data

(60) Provisional application No. 61/029,324, filed on Feb. 16, 2008.

(51) Int. Cl.
*A61B 5/055* (2006.01)

(52) U.S. Cl.
USPC ............ 600/421; 600/407; 600/410; 600/411

(58) Field of Classification Search
None
See application file for complete search history.

(56) References Cited

U.S. PATENT DOCUMENTS

| | | | | |
|---|---|---|---|---|
| 5,521,502 A * | 5/1996 | Siegel et al. | ................. | 324/306 |
| 5,524,636 A * | 6/1996 | Sarvazyan et al. | ............ | 600/587 |
| 5,592,085 A | 1/1997 | Ehman | | |
| 5,606,971 A | 3/1997 | Sarvazyan | | |
| 5,810,731 A | 9/1998 | Sarvazyan et al. | | |
| 5,916,180 A * | 6/1999 | Cundari et al. | ............... | 600/587 |
| 5,952,828 A | 9/1999 | Rossman et al. | | |
| 5,977,770 A | 11/1999 | Ehman | | |
| 6,037,774 A * | 3/2000 | Felmlee et al. | ............... | 324/318 |
| 6,486,669 B1 | 11/2002 | Sinkus et al. | | |
| 6,833,703 B2 * | 12/2004 | Sinkus et al. | ................. | 324/318 |
| 7,901,355 B2 * | 3/2011 | Querleux et al. | ............ | 600/438 |
| 2002/0112476 A1 | 8/2002 | Truninger | | |
| 2005/0270029 A1 * | 12/2005 | Ehman et al. | ................. | 324/318 |
| 2011/0006767 A1 * | 1/2011 | Sack et al. | .................... | 324/309 |

OTHER PUBLICATIONS

International Search report of PCT/CN2009/070417.
Hong Kong Short-term Patent Search Report.

\* cited by examiner

*Primary Examiner* — Long V. Le
*Assistant Examiner* — Bradley Impink

(57) ABSTRACT

A hydraulic driver of a magnetic resonance elastography (MRE) system is provided. The hydraulic driver is adapted to be connected to at least a passive actuator for contacting with a subject. The hydraulic driver includes a pump, a hydraulic piston-cylinder unit operatively coupled to the pump, and a tube assembly. The tube assembly includes a proximal end in fluid communication with the hydraulic piston-cylinder unit and a distal end in fluid communication with the passive actuator. The passive actuator oscillates in response to hydraulic energy generated in a fluid in the hydraulic driver as the pump drives the piston forward and backward in the cylinder of the hydraulic piston-cylinder unit.

14 Claims, 8 Drawing Sheets

MAGNETIC RESONANCE ELASTOGRAPH SYSTEM WITH HYDRAULIC DRIVER

CROSS-REFERENCE TO RELATED PATENT APPLICATIONS

This patent application claims the benefit of U.S. provisional application No. 61/029,324, filed on Feb. 16, 2008, the entire contents of which are hereby incorporated by reference.

FIELD OF PATENT APPLICATION

The present patent application relates to a magnetic resonance elastography system with a hydraulic driver.

BACKGROUND

There are many diagnostic tools which can help physician to detect and localize the diseased tissues. Many diseased tissues are detected by the physical properties measured by imaging modalities, but many diseases may go undetected. Magnetic resonance elastography (MRE) can cover those undetected diseases such as early detection of small tumor, carcinoma, cirrhosis, arteriosclerosis, lymphedema, mild cognitive impairment (MCI) or related brain diseases, or FDA new drug testing in the below-mentioned ways.

MRE detects "atomic density change" with very high resolution. Diseased tissue changes its "elasticity" and "density" before its "shape change." Elastography can detect either "elasticity change" or "density change" of tissues before "shape change". MRE can detect diseased tissue before its "shape change", which can be detected using other diagnostic tools such as X-ray, CT, ultrasound, PET and magnetic resonance imaging (MRI). MRE can detect diseased tissue before its "function, enzymes, chemistry, electrolytes, lipids and protein changes", which can be detected by blood tests such as liver function, liver enzymes, liver chemistry, liver electrolytes, liver lipids and liver protein. Early detection improves effectiveness of treatments. MRE improves early detection capability including (a) small size of "shape changes"; (b) some other physical property changes before "shape changes"; (c) some other physical property changes before "function, enzymes, chemistry, electrolytes, lipids and protein changes"; and (d) small size of "some other physical property changes".

Historically, one of the physician's most valuable diagnostic tools is palpation. By palpating the patient a physician can feel differences in the compliance of tissues and detect the presence of tumors and other tissue abnormalities. Unfortunately, this valuable diagnostic tool is limited to those tissues and organs which the physician can feel, and many diseased internal organs go undiagnosed unless the disease happens to be detectable by one of the conventional imaging modalities. The stiffness of tumors, (e.g. of the liver and the brain) which are undetected by existing imaging modalities and cannot be reached for palpation through the patient's skin and musculature, are often detected by surgeons by direct palpation of the exposed organs at the time of surgery. Palpation is the most common means of detecting enlargement of lymph glands and tumors of the prostate gland and the breast. Unfortunately, deeper portions of these structures are not accessible for such evaluation. An imaging system that extends the physician's ability to detect differences in tissue compliance throughout a patient's body would extend this valuable diagnostic tool.

MRI can be enhanced when an oscillating stress is applied to a subject being imaged by MRE method. The method requires that the oscillating stress produce shear waves that propagate through the organ, or tissues to be imaged. These shear waves alter the phase of the nuclear resonance imaging (NMR) signals, and from this the mechanical properties of the subject can be determined. In many applications, the production of shear waves in the tissues is merely a matter of physically vibrating the surface of the subject with an electromechanical device. For example, shear waves may be produced in the breast and prostate by direct contact with the oscillatory device. Also, with organs like the stomach and uterus, the oscillatory force can be directly applied by means of an applicator that is inserted into the organ.

MRE early detection depends on its driver. A number of driver devices have been developed to produce the oscillatory force needed to practice MRE. Electromechanical driver devices typically include a coil of wire through which an oscillating current flows. To create an oscillating current flow, the coil has to be oriented in the polarizing magnetic field of a MRI system to avoid the interactions with the magnetic field. The force of oscillating current flows may be conveyed to the subject being imaged by any number of different mechanical arrangements. Such MRE drivers can produce large forces over large displacement, but they are constrained by the need to keep the coil properly aligned with respect to the polarizing magnetic field. In addition, the current flowing in the driver coil produces a magnetic field which can alter the magnetic fields during the magnetic resonance pulse sequence resulting in undesirable image artifacts. It is also easy to burn out during the magnetic resonance (MR) scan due to the eddy current, especially in the higher field MR system such as in a 3 T MR system.

Another approach is the employment of piezoelectric drivers. Piezoelectric drivers can also be oriented in any direction since they are not dependent on the polarizing magnetic field direction for proper operation. Such drivers do not produce troublesome disturbances in the scanner magnetic fields when operated, but they are limited in the forces they can produce, particularly at larger displacements. It's easy to break under increased force due to the thin and brittle material.

A further approach is the employment of pneumatic drivers. Pneumatic driver produces large forces and can be oriented in any direction inside the MR system. While there are no artifacts, it is hard to put in the position due to the hard tube and hard passive actuator. A subject will feel very uncomfortable when putting the hard passive actuator on some regions of the subject, especially for the brain. The stimulation frequency and power at the end of the pneumatic driver are unknown. Also, the power is attenuated seriously due to the long tube.

The above description of the background is provided to aid in understanding the hydraulic driver for magnetic resonance elastography disclosed in the present application, but is not admitted to describe or constitute pertinent prior art to the hydraulic driver for magnetic resonance elastography, or consider any references as material to the patentability of the claims of the present application.

SUMMARY

A magnetic resonance elastography (MRE) system includes a hydraulic driver adapted to produce hydraulic energy that oscillates a subject such as a human.

The hydraulic driver is adapted to be connected to at least a passive actuator for contacting with the subject. The hydraulic driver includes a pump, a hydraulic piston-cylinder unit operatively coupled to the pump, and a tube assembly. The tube assembly includes a proximal end in fluid communication with the hydraulic piston-cylinder unit and a distal end in fluid communication with the passive actuator. The passive actuator oscillates in response to hydraulic energy generated in a fluid in the hydraulic driver as the pump drives the piston forward and backward in the cylinder of the hydraulic piston-cylinder unit.

The tube assembly may include at least a flexible hose having a proximal end and a distal end, and the passive actuator is hydraulically coupled to the distal end of the flexible hose.

The tube assembly may include a tube connector having at one end thereof an opening for fluid communication with a tube extending from the piston-cylinder unit, and at an opposite end thereof at least an opening for fluid communication with the proximal end of the flexible hose.

The flexible hose and the passive actuator are sized and shaped for insertion into an internal portion of the human.

The tube assembly may include a reservoir having at one end thereof an opening for fluid communication with a first tube extending from the piston-cylinder unit, and at an opposite end thereof an opening for fluid communication with a second tube leading to the passive actuator.

The hydraulic driver may include a controller for controlling the pump. The passive actuator may include a pressure sensor for measuring pressure and providing a feedback signal to the controller. The passive actuator may include a frequency sensor for measuring frequency and providing a feedback signal to the controller.

The fluid in the hydraulic driver produces a dark background in MRE images.

BRIEF DESCRIPTION OF THE DRAWINGS

FIGS. 7 (e)-(h) are cross sectional views of the four tube connectors in FIGS. 7 (a)-(d) respectively.

DETAILED DESCRIPTION

Reference will now be made in detail to a preferred embodiment of the hydraulic driver for magnetic resonance elastography disclosed in the present application, examples of which are also provided in the following description. Exemplary embodiments of the hydraulic driver disclosed in the present application are described in detail, although it will be apparent to those skilled in the relevant art that some features that are not particularly important to an understanding of the hydraulic driver may not be shown for the sake of clarity.

Furthermore, it should be understood that the MRE system disclosed in the present patent application is not limited to the precise embodiments described below and that various changes and modifications thereof may be effected by one skilled in the art without departing from the spirit or scope of the appended claims. For example, elements and/or features of different illustrative embodiments may be combined with each other and/or substituted for each other within the scope of this disclosure and appended claims.

In addition, improvements and modifications which may become apparent to persons of ordinary skill in the art after reading this disclosure, the drawings, and the appended claims are deemed within the spirit and scope of the appended claims.

It should be noted that throughout the specification and claims herein, when one element is said to be "coupled" or "connected" to another, this does not necessarily mean that one element is fastened, secured, or otherwise attached to another element. Instead, the term "coupled" or "connected" means that one element is either connected directly or indirectly to another element, or is in mechanical, electrical, or fluid communication with another element.

As used herein, the term "distal end" refers to an end towards a subject in a magnetic resonance scanner room, and the term "proximal end" refers to an end opposite to the "distal end" away from the subject. As used herein, the term "subject" refers to an animal or a human.

Figure 1:
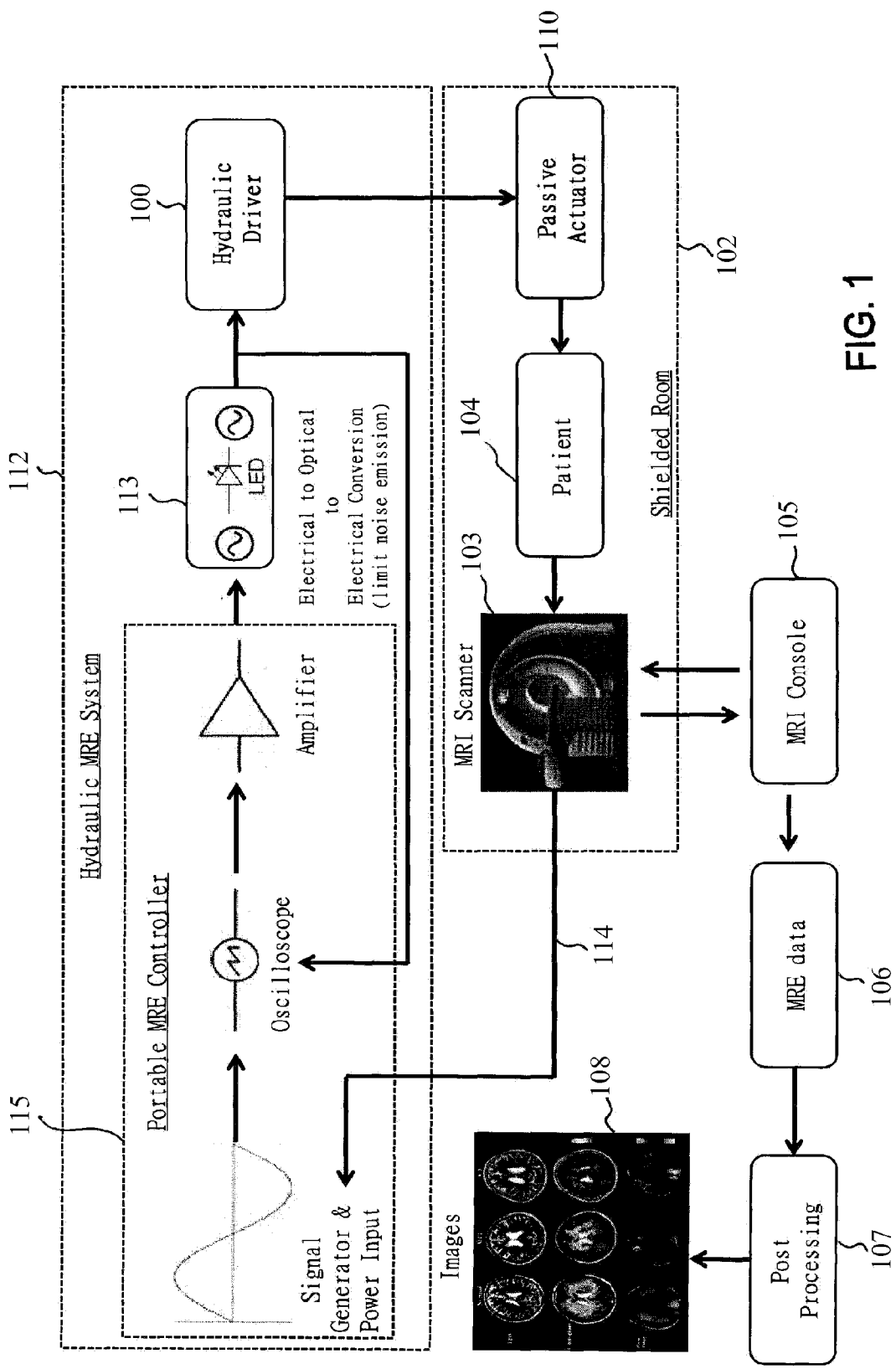
FIG. 1 shows a block diagram of the implementation of a hydraulic driver for use in a MRE system according to an embodiment disclosed in the present patent application.

FIG. 1 shows a block diagram of the implementation of a hydraulic driver 100 for use in a MRE system 112 according to an embodiment disclosed in the present patent application.

The MRE system 112 includes a hydraulic driver 100, which is hydraulically coupled to at least a passive actuator 110 in a shielded room of a MRI system 102. The hydraulic driver 100 is located outside the shielded room. The passive actuator 110 can be positioned on a surface of a patient 104 or in an internal organ or even a vessel of the patient 104 inside the shielded room of the MRI system 102. The patient 104 can be sent into a MRI scanner 103 for MRI scanning. The MRI scanner 103 inside the shielded room of the MRI system 102 is controlled by a MRI console 105. The operation of the MRE system 112 via the MRI scanner 103 produces MRE data 106, which is processed by post-processing software 107 to produce both MRE wave images and elastogaphy 108 that may be graphically viewed on a display device.

The hydraulic driver 100 of the MRE system 112 uses signals that are produced by a signal component (MRE controller) 115 which may be portable. The signal component 115 includes a generator for the generation of a signal, an oscilloscope for the display of the signal from the generator, and an amplifier for increasing the power of the signal. The signal generation of the generator can be synchronized with the operation of the MRI scanner 103 through a signal line (trigger) 114. Typical frequencies are 40-1000 Hz. The signal duration lasts through the MRE scan.

The MRE system 112 may also include an electrical-optical-electrical converter 113. The hydraulic driver 100 requires an electric signal to operate. However, using metal wire to provide the signal may induce interference in the signal, because the metal wire will inductively receive EM fields generated by the MRI scanner 103. Thus, the MRI scanner 103 can interfere with the operation of the hydraulic driver 100. The signal leaving the amplifier is converted to an optical signal by the converter 113. Such a conversion may be accomplished by using an LED or OLED or an LED laser. The light signal is then carried on a fiber optic wire to the hydraulic driver 100.

Large oscillatory forces can be produced on the patient 104 during a MRE scan without interfering with the operation of the MRI system 102. The oscillatory force can be produced by the hydraulic driver 100 of the MRE system 112 which is located remotely from the MRI system 102 magnetic fields. The source of energy comes from the hydraulic driver that generates an acoustic shear wave. Thus, any mechanical excitations that may be produced by the hydraulic driver will not interfere with the operation of the MRI scanner 103.

The passive actuator 110 may be oriented in any direction on a surface of the patient 104 or in an internal organ of the patient 104 with reliability, durability, sensitivity, less attenuation, and more comfort. The hydraulic driver 100 of the MRE system 112 is easy to setup and use.

Figure 2:
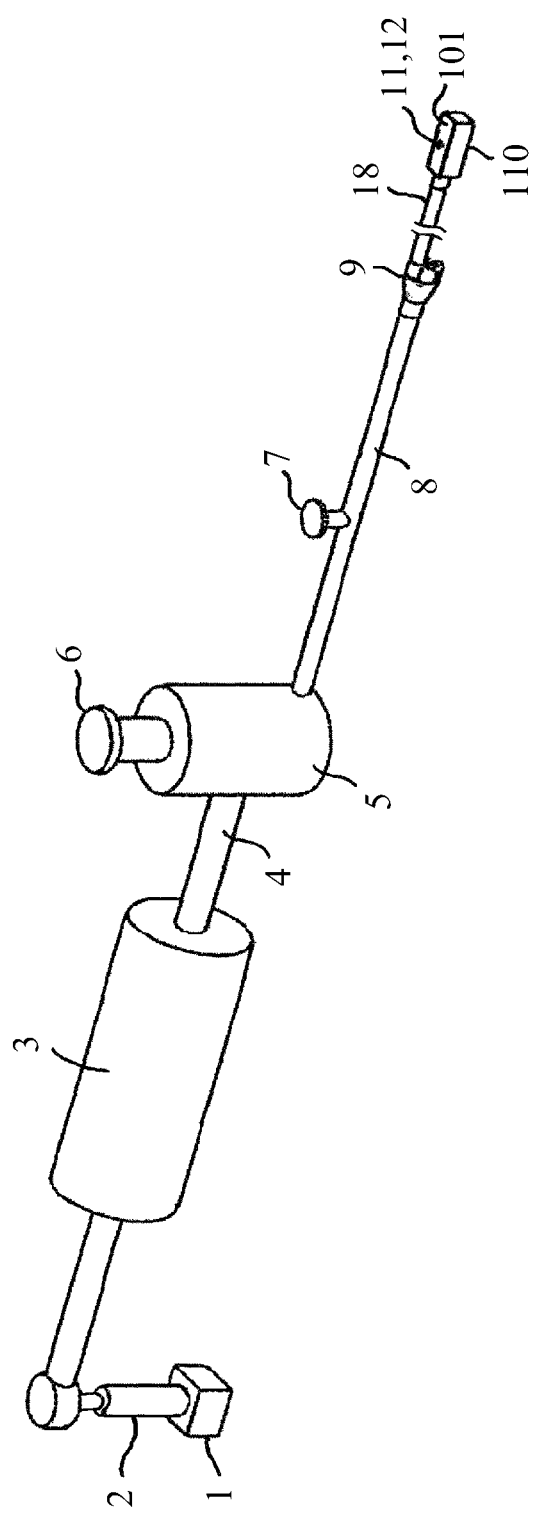
FIG. 2 shows a perspective view of a hydraulic driver and a passive actuator according to an embodiment of the present application.
Figure 3:
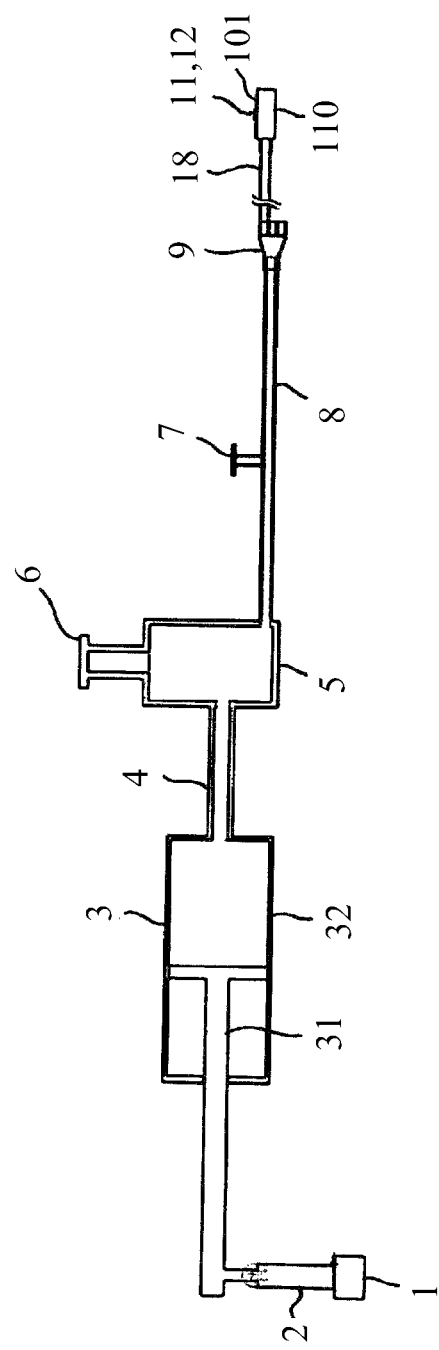
FIG. 3 shows a cross sectional view of the hydraulic driver and the passive actuator of FIG. 2.

FIGS. 2 and 3 show the hydraulic driver and the passive actuator for magnetic resonance elastography according to an embodiment disclosed in the present patent application.

The hydraulic driver may include a pump 2 and a controller 1 for controlling the pump 2. A hydraulic piston-cylinder unit 3 is operatively coupled to the pump 2. The hydraulic piston-cylinder unit 3 has a working piston 31 and a hydraulic cylinder 32, which is filled with hydraulic fluid. The working piston 31 can move forward and backward in the hydraulic cylinder 32 to generate hydraulic energy by the hydraulic fluid in the hydraulic driver. The controller 1, the pump 2 and the hydraulic piston-cylinder unit 3 can be located at a proximal end of the hydraulic driver outside the shielded room of the MRI system 102.

The passive actuator 110 of the MRI system may have a membrane 101 for contacting with a surface of a subject or for insertion into an internal organ or even a vessel of the subject such as a human. The passive actuator 110 can be attached to a distal end of the hydraulic driver and located inside the shielded room of the MRI system 102. The membrane 101 oscillates in response to hydraulic energy generated in the fluid in the hydraulic driver as the pump 2 drives the piston 31 forward and backward in the cylinder 32 of the hydraulic piston-cylinder unit 3.

The hydraulic driver includes a tube assembly for hydraulically coupling the hydraulic piston-cylinder unit 3 with the passive actuator 110. The tube assembly has a proximal end portion in fluid communication with the hydraulic piston-cylinder unit 3 and a distal end in fluid communication with the passive actuator 110. The fluid in the hydraulic piston-cylinder unit 3, the tube assembly, and the passive actuator 110 may be oil, preferably oil sold under the trademark Fomblin, or any other fluid which is able to produce a dark background in the MRE images. If water is used, an undesirable light background in the MRE images will be produced.

According to an embodiment disclosed in the present patent application, the tube assembly has at least a flexible hose 18 having a proximal end and a distal end. The passive actuator 110 is provided at the distal end of the flexible hose 18. The passive actuator 110 and the flexible hose 18 may be made of plastic such as polycarbonate or any materials which do not substantially perturb magnetic fields produced in the MRI system 102. The flexible hose 18 may pass through a bore of the MRI scanner room and may have a length sufficient to connect the passive actuator 110 inside the scanner room 102 to the hydraulic piston-cylinder unit 3 outside the scanner room. The flexible hose 18 and the actuator 110 can be sized and shaped for positioning on a surface of a subject or for insertion into an internal organ or even a vessel of the subject such as a human.

The tube assembly may include a tube connector 9. The tube connector 9 may have at one end thereof an opening in fluid communication with a tube 8 extending from the piston-cylinder unit 3, and at an opposite end thereof an opening in fluid communication with the proximal end of the flexible hose 18.

The tube assembly may have a reservoir 5 having at one end thereof an opening in fluid communication with a tube 4 connecting to the piston-cylinder unit 3, and at an opposite end thereof an opening in fluid communication with the tube 8 leading to the passive actuator 110. It can be seen that the diameter of the tube 4 is larger than the diameter of the tube 8. This can increase the pressure of fluid as it moves from the tube 4 to the tube 8 through the reservoir 5. A valve 6 may be provided on the reservoir 5 to facilitate the addition of fluid therein and regulating the fluid in the hydraulic driver.

A gas-releasing valve 7 may be provided on the tube 8 for the release of gas that may be formed therein. The gas-releasing valve 7 may be provided on any other position of the hydraulic drive if appropriate.

A pressure sensor 11 and a frequency sensor 12 can be removably attached to the membrane 101 for measuring its pressure and frequency, and providing a feedback signal to the controller 1 for necessary adjustment. This ensures safe and proper operation of the hydraulic driver.

Figure 4:
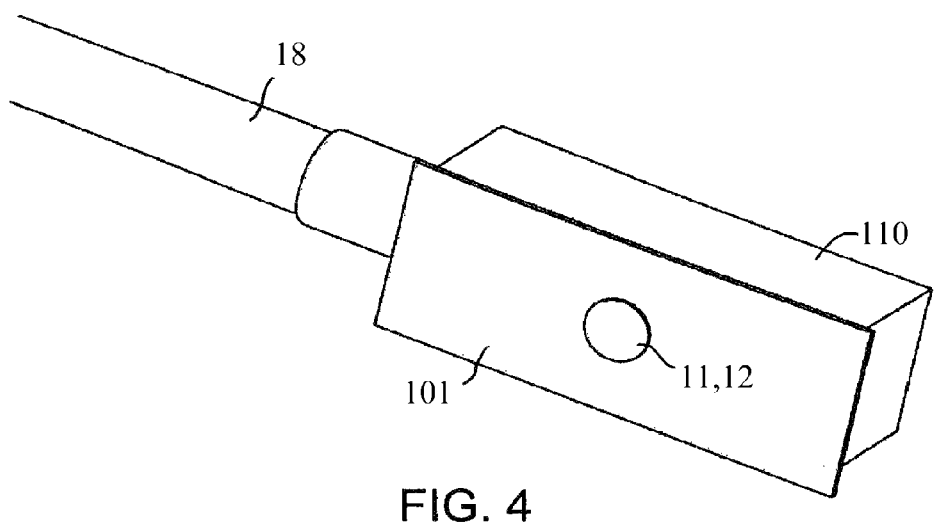
FIG. 4 is an enlarged perspective view of the passive actuator of FIG. 2.
Figure 5:
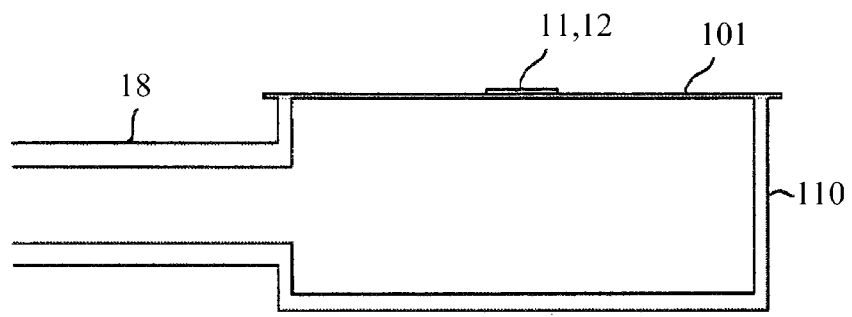
FIG. 5 is a cross sectional view of the passive actuator of FIG. 4.
Figure 6:
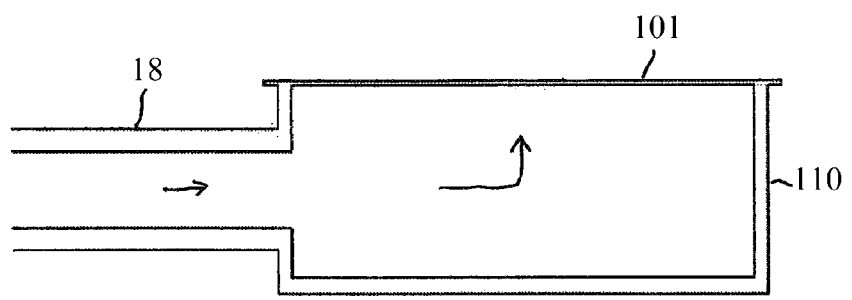
FIG. 6 is a cross sectional view of the passive actuator of FIG. 4 with a pressure sensor or a frequency sensor removed therefrom.

FIGS. 4, 5 and 6 show the passive actuator 110 according to an embodiment disclosed in the present application. The passive actuator 110 is hydraulically coupled to the distal end of the flexible hose 18. According to the illustrated embodiment, the passive actuator 110 has a membrane 101 extending across an opening of the passive actuator 110. The membrane 101 may be made of plastic or any other suitable material.

Oscillation of the hydraulic driver can be transmitted through fluid in the flexible hose 18 to the fluid in the passive actuator 110 causing the soft membrane 101 to oscillate. The membrane 101 bears against a subject and applies a corresponding oscillatory force to the subject. This kind of passive actuator can be suitable for applying oscillatory force on a surface of a subject.

It is understood by one skilled in the art that the passive actuator 110 of the hydraulic driver can be in any suitable forms so long as it can bear against a surface of a subject and produce the necessary oscillatory force on the contacting surface. For example, the passive actuator 110 may be in the form of a soft plastic sack. The soft plastic sack can be hydraulically coupled to the distal end of the flexible hose 18. Oscillation of the hydraulic driver can be transmitted through fluid in the flexible hose 18 to the fluid in the sack. The sack bears against the subject and applies a corresponding oscillatory force to the subject. This kind of passive actuator can be suitable for insertion into internal organs of a subject.

The passive actuator 110 may also be in the form of an elastic tube which can expand and contract in diameter in response to the hydraulic energy. This kind of passive actuator can be suitable for wrapping around an appendage of a subject.

Before MRE operation on the subject is performed, the pressure sensor 11 and the frequency sensor 12 can be attached onto the membrane 101, as shown in FIG. 5, to measure its pressure and frequency. If the pressure or the frequency is too high or too low as compared to the set pressure/frequency, then a feedback signal will be sent to the controller 1 for necessary adjustment. If both the pressure and frequency meet the requirements of the operation, the pressure sensor 11 and the frequency sensor 12 can be removed from the membrane 101, as shown in FIG. 6. The membrane 101 can then be attached to the subject. The arrows indicate the directions of fluid propagation inside the passive actuator 110.

Figure 7:
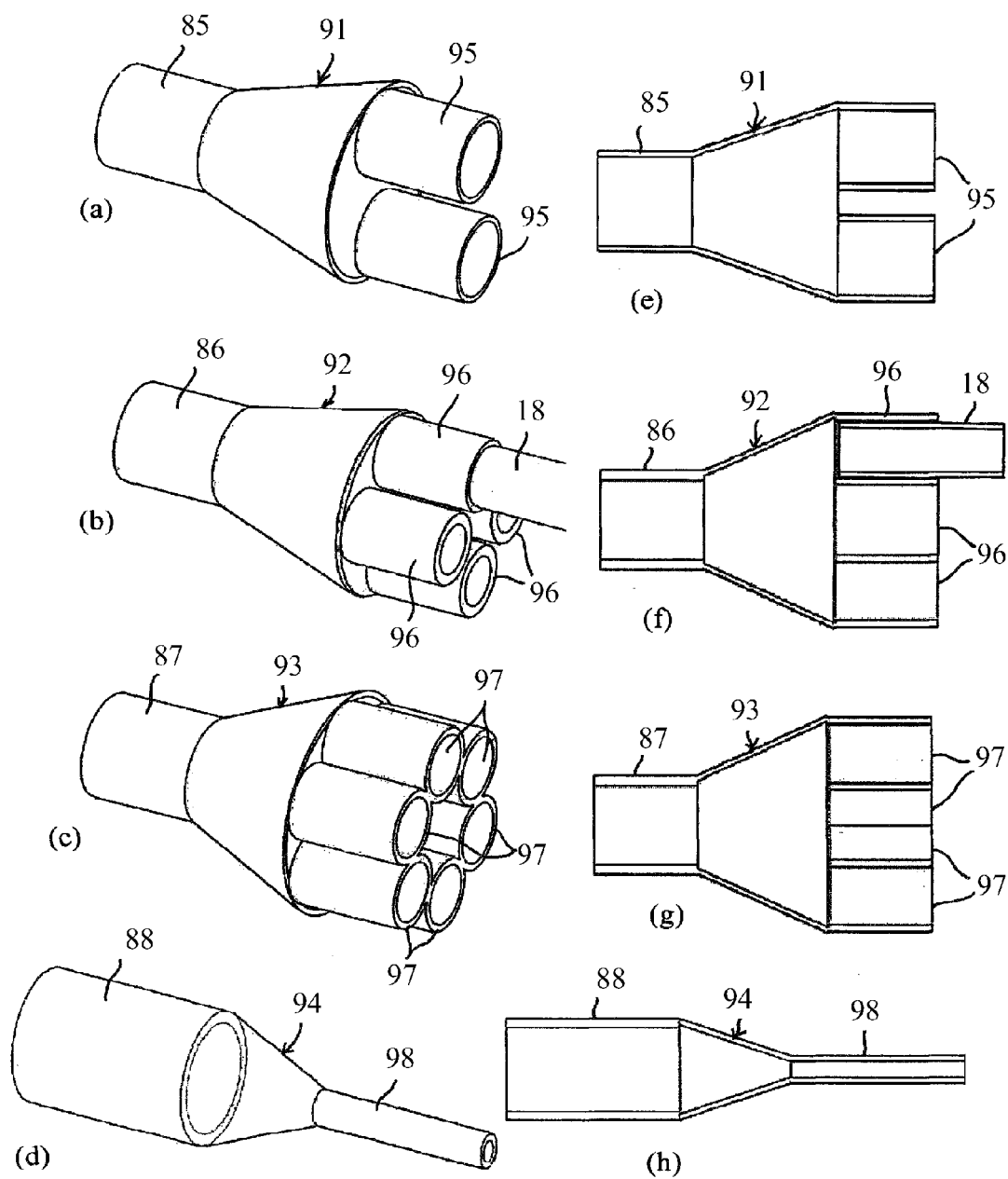
FIGS. 7 (a)-(d) are perspective views of four embodiments of a tube connector of the hydraulic driver disclosed in the present application.

FIGS. 7 (a)-(h) show four embodiments of the tube connector 9 disclosed in the present application.

As shown in the first embodiment in FIGS. 7(a) and 7(e), a tube connector 91 has at one end thereof an opening defined by a tubular member 85 for fluid communication with the tube 8, and at the opposite end thereof two openings defined by two tubular members 95 for fluid communication with the proximal ends of two flexible hoses 18 respectively. The tube 8 and the two flexible hoses 18 may be fixedly connected to the tube connector 91 to form a twin hydraulic driver.

As shown in the second embodiment in FIGS. 7(b) and 7(f), a tube connector 92 has at one end thereof an opening defined by a tubular member 86 for fluid communication with the tube 8, and at the opposite end thereof four openings defined by four tubular members 96 for fluid communication with the proximal ends of four flexible hoses 18 respectively. FIGS. 7(b) and 7(f) illustrate the insertion of one flexible hose 18 into one tubular member 96 of the tube connector 92. The flexible hose 18 can be secured in the tubular member 96 of the tube connector 92 by any conventional fastening and/or sealing means to form a four hydraulic driver.

As shown in the third embodiment in FIGS. 7(c) and 7(g), a tube connector 93 has at one end thereof an opening defined by a tubular member 87 for fluid communication with the tube 8, and at the opposite end thereof six openings defined by six tubular members 97 for fluid communication with the proximal ends of six flexible hoses 18 respectively. The tube 8 and the flexible hoses 18 may be fixedly connected to the tube connector 91 to form a multiple hydraulic driver.

It is appreciated that the hydraulic driver may have only one flexible hose 18. As shown in the fourth embodiment in FIGS. 7(d) and 7(h), a tube connector 94 has at one end thereof an opening defined by a tubular member 88 for fluid communication with the tube 8, and at the opposite end thereof one opening defined by a tubular member 98 for fluid communication with the proximal end of one flexible hose 18 to form a single hydraulic driver.

It is understood that the flexible hoses 18 of the twin or multiple hydraulic driver can be inserted into different regions of an internal organ, or can be inserted into different internal organs of a subject so that a plurality of passive actuators 110 may be positioned at different locations of the subject for possible simultaneous operation.

Figure 8:
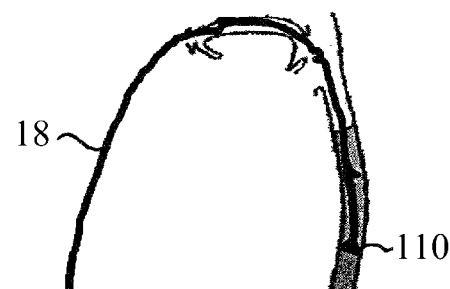
FIG. 8 shows two hydraulic drivers used for a digestive system such as esophagus and intestine, respectively.
Figure 8:
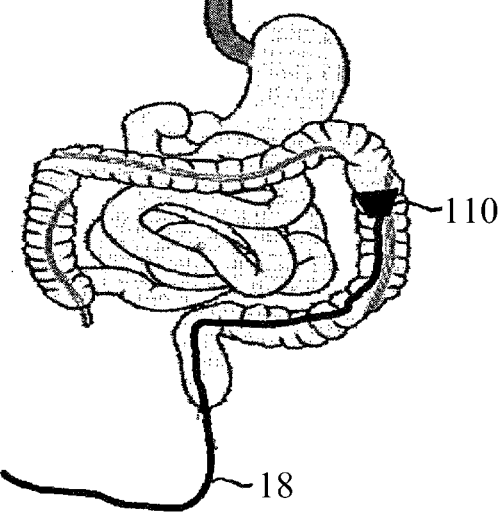

FIG. 8 shows the use of two hydraulic drivers for the examination of different portions of a digestive system such as esophagus and intestine. The hydraulic drivers have two flexible hoses 18 and two passive actuators 110 respectively. One flexible hose 118 is inserted into the esophagus and the other flexible hose 18 is inserted into the intestine, respectively. It can be seen that the two passive actuators 110 at the distal ends of the two flexible hoses 18 are of different sizes according to the size of organs.

Figure 9:
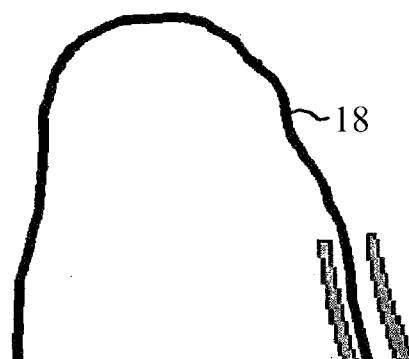
FIG. 9 shows a single hydraulic driver used for stomach such as oesophagus, cardiac sphincter, fundus, middle, pylorus, pyloric sphincter and duodenum.
Figure 9:
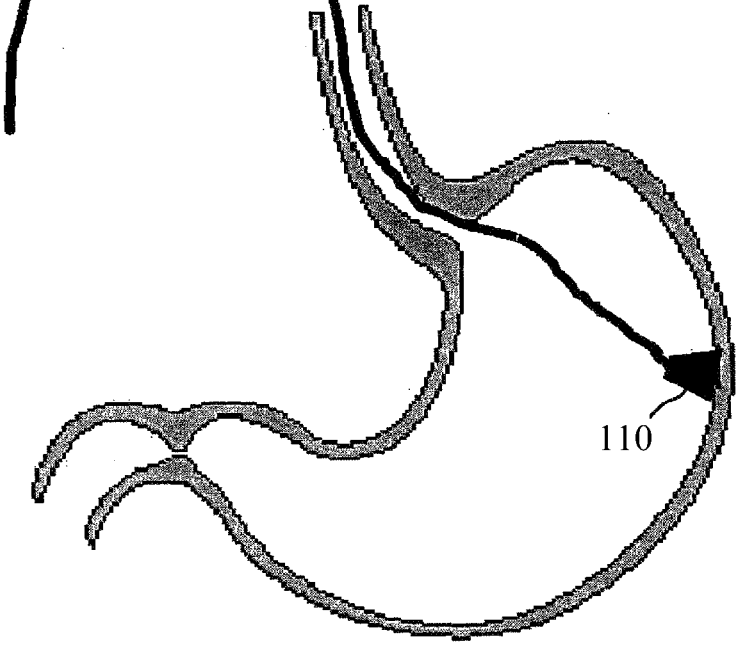

FIG. 9 shows the use of a single hydraulic driver for the examination of different portions of a stomach such as esophagus, cardiac sphincter, fundus, middle, pylorus, pyloric sphincter and duodenum. This single hydraulic driver has one flexible hose 18 for insertion into the stomach of the subject and one passive actuator 110 at a distal end for the examination of different regions in the stomach.

Figure 10:
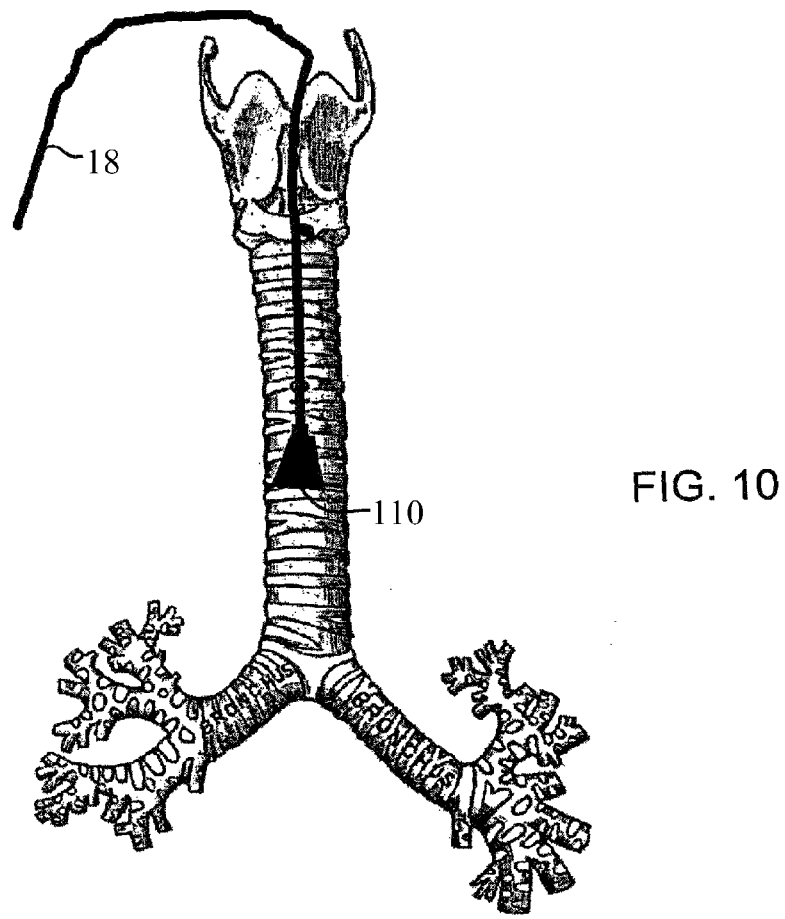
FIG. 10 shows a single hydraulic driver used for trachea.

FIG. 10 shows the use of a single hydraulic driver for the examination of a trachea. Again, this single hydraulic driver has one flexible hose 18 for insertion into the trachea of the subject and one passive actuator 110 at a distal end for the examination of different regions of the trachea.

Figure 11:
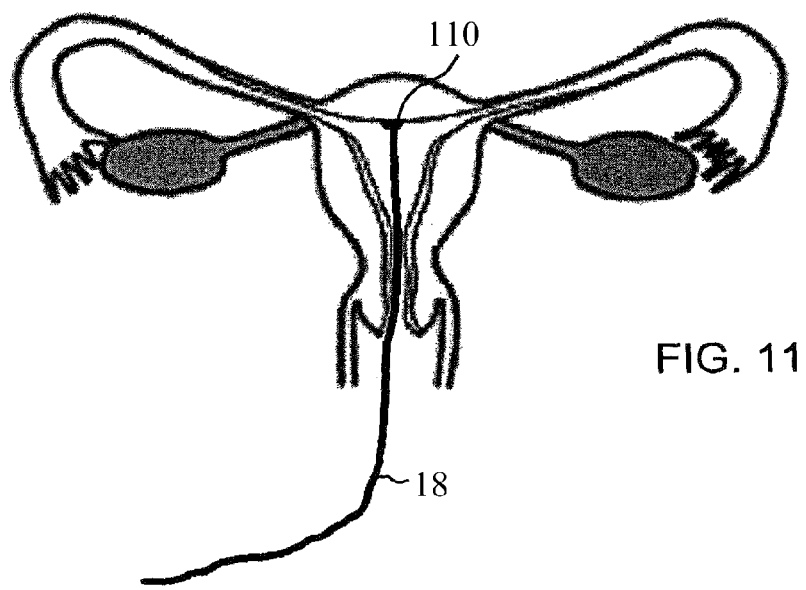
FIG. 11 shows a single hydraulic driver used for uterus, fallopian tubes, ovary, cervix and vagina.

FIG. 11 shows the use of a single hydraulic driver for the examination of uterus, fallopian tubes, ovary, cervix and vagina for early detection of genital cancer or tumor. Again, this single hydraulic driver has one flexible hose 18 for insertion into the uterus of the subject and one passive actuator 110 at a distal end for the examination of different regions of the uterus.

Figure 12:
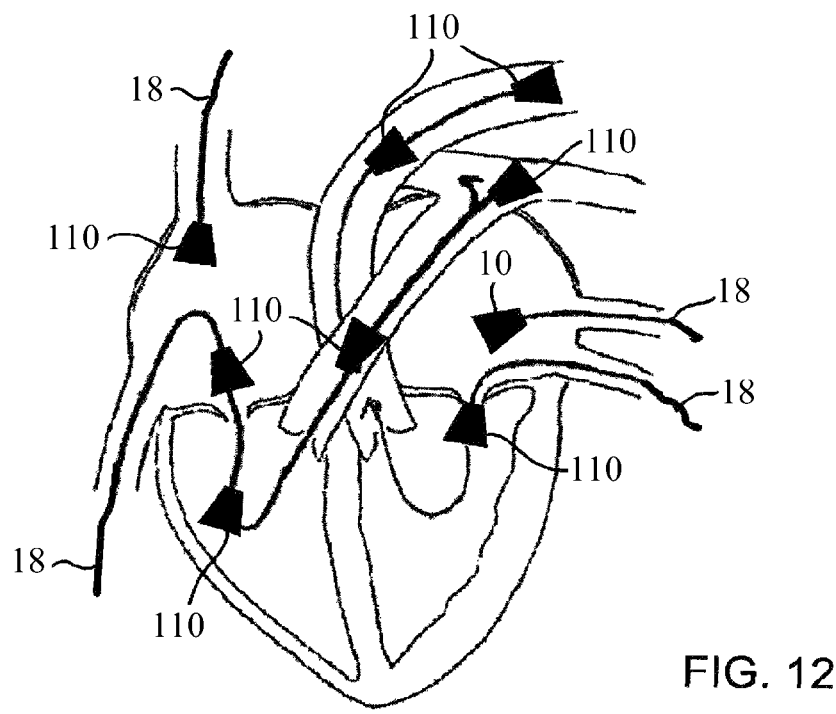
FIG. 12 shows a multiple hydraulic driver used for cardiac muscle and vascular wall such as right and left atrium, right and left ventricle, inferior vena cava, superior vena cava, pulmonary vein, pulmonary artery and aorta.

FIG. 12 shows the use of a multiple hydraulic driver for the examination of different portions of a heart including cardiac muscle and vascular wall such as right and left atrium, right and left ventricle, inferior vena cava, superior vena cava, pulmonary vein, pulmonary artery and aorta. The multiple hydraulic drivers have a plurality of flexible hoses 18, each having one or more passive actuators 110 hydraulically coupled to the distal end thereof. The flexible hoses 18 can reach the right atrium via superior vena cava or inferior vena cava, or the right ventricle and pulmonary artery via right atrium, or the left atrium, left ventricle and aorta via pulmonary vein.

Figure 13:
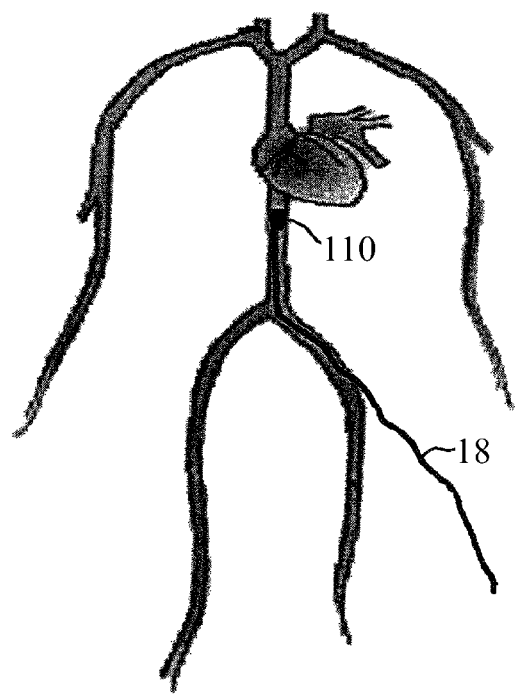
FIG. 13 shows a single hydraulic driver used for vascular system such as carotid artery, subclavian artery, celiac trunk, mesenteric arteries, renal artery and iliac artery; and subclavian vein, jugular vein, renal vein and iliac vein.

FIG. 13 shows the use of a single hydraulic driver for the examination of different portions of a vascular system such as carotid artery, subclavian artery, celiac trunk, mesenteric arteries, renal artery, iliac artery, subclavian vein, jugular vein, renal vein and iliac vein to detect arteriosclerosis at early stage. This single hydraulic driver has one flexible hose 18 for insertion into the vascular system of the subject and one passive actuator 110 at a distal end thereof. It is appreciated that the size of the passive actuator 110 for the examination of the vascular system is much smaller than the size of the passive actuator for the examination of other larger internal organs such as the stomach.

There may be four major applications in medicine. The first application is in tumor detection. The guess work of the surgeon in finding out a tumor with palpation is replaced by high quality precision 3D imaging using MRI scanners. The second application is the early detection of the liver cirrhosis before the abnormal liver function, enzymes, chemistry, lipids and protein which can be detected by blood test. The third application is the early detection of the hardening of arteries, a major disease that has no known method of diagnosis except by secondary effects or surgery. The forth application is for early detection of Alzheimer's (AD) or related brain diseases. From autopsy, it is known that the AD brain is structurally different from the normal ones, i.e. beta-amyloid plagues and fibrillar tangles are found. All the applications are based on disease-caused changes of elasticity of tissue. While tumor and live cirrhosis diagnosis has been reported in the literature, the third and four applications are not reported although it's obvious.

The hydraulic driver for magnetic resonance elastography disclosed in the present application is adapted for sensitive and specific detection of mild cognitive impairment (MCI), Alzheimer's disease (AD), liver cirrhosis, arteriosclerosis, lymph edema and tumors of breast, liver, kidney and prostate. It uses invasive hydraulic driver for stiffness analysis of the digestive system such as esophagus, stomach and intestine, as well as trachea. It may also detect genital cancer or tumor such as uterus, fallopian tubes, ovary, cervix and vagina.

While the hydraulic driver for magnetic resonance elastography disclosed in the present application has been shown and described with particular references to a number of preferred embodiments thereof, it should be noted that various other changes or modifications may be made without departing from the scope of the appended claims.

What is claimed is:

1. A hydraulic driver of a magnetic resonance elastography (MRE) system, wherein the hydraulic driver is adapted to be connected to at least a passive actuator for contacting with a subject, the hydraulic driver comprising:
    a pump;
    a hydraulic piston-cylinder unit operatively coupled to the pump; and
    a tube assembly comprising a proximal end in liquid communication with the hydraulic piston-cylinder unit and a distal end in liquid communication with the passive actuator;
    wherein the passive actuator oscillates in response to hydraulic energy generated in a liquid in the hydraulic driver as the pump drives the piston forward and backward in the cylinder of the hydraulic piston-cylinder unit; and
    wherein the tube assembly comprises a reservoir having at one end thereof an opening for liquid communication with a first tube extending from the piston-cylinder unit, and at an opposite end thereof an opening for liquid communication with a second tube leading to the passive actuator; a diameter of the first tube is larger than a diameter of the second tube;
    and a valve is provided on the reservoir.

2. The hydraulic driver as claimed in claim 1, wherein the tube assembly comprises at least a flexible hose comprising a proximal end and a distal end, and the passive actuator is hydraulically coupled to the distal end of the flexible hose.

3. The hydraulic driver as claimed in claim 2, wherein the tube assembly comprises a tube connector comprising at one end thereof an opening for liquid communication with a tube extending from the piston-cylinder unit, and at an opposite end thereof at least an opening for liquid communication with the proximal end of the flexible hose.

4. The hydraulic driver as claimed in claim 2, wherein the flexible hose is sized and shaped for insertion into an internal portion of the subject.

5. The hydraulic driver as claimed in claim 1, further comprising a controller for controlling the pump, and wherein the passive actuator comprising a pressure sensor for measuring pressure and providing a feedback signal to the controller.

6. The hydraulic driver as claimed in claim 1, further comprising a controller for controlling the pump, and wherein the passive actuator comprising a frequency sensor for measuring frequency and providing a feedback signal to the controller.

7. A magnetic resonance elastography (MRE) system comprising a hydraulic driver adapted to produce hydraulic energy that oscillates a subject;
    wherein the hydraulic driver is connected to at least a passive actuator, and the hydraulic driver comprises:
        a pump;
        a hydraulic piston-cylinder unit operatively coupled to the pump; and
        a tube assembly comprising a proximal end in liquid communication with the hydraulic piston-cylinder unit and a distal end in liquid communication with the passive actuator;
    wherein the passive actuator oscillates in response to hydraulic energy generated in a liquid in the hydraulic driver as the pump drives the piston forward and backward in the cylinder of the hydraulic piston-cylinder unit; and
    wherein the tube assembly comprises a reservoir having at one end thereof an opening for liquid communication with a first tube extending from the piston-cylinder unit, and at an opposite end thereof an opening for liquid communication with a second tube leading to the passive actuator; a diameter of the first tube is larger than a diameter of the second tube;
    and a valve is provided on the reservoir.

8. The MRE system as claimed in claim 7, wherein the tube assembly comprises at least a flexible hose comprising a proximal end and a distal end, and the passive actuator is hydraulically coupled to the distal end of the flexible hose.

9. The MRE system as claimed in claim 8, wherein the tube assembly comprises a tube connector comprising at one end thereof an opening for liquid communication with a tube extending from the piston-cylinder unit, and at an opposite end thereof at least an opening for liquid communication with the proximal end of the flexible hose.

10. The MRE system as claimed in claim 8, further comprising a tube connector comprising at least an opening for liquid communication with the proximal end of the flexible hose.

11. The MRE system as claimed in claim 8, wherein the flexible hose and the passive actuator are sized and shaped for insertion into an internal portion of the subject.

12. The MRE system as claimed in claim 7, further comprising a controller for controlling the pump, and wherein the passive actuator comprising a pressure sensor for measuring pressure and providing a feedback signal to the controller.

13. The MRE system as claimed in claim 7, further comprising a controller for controlling the pump, and wherein the passive actuator comprising a frequency sensor for measuring frequency and providing a feedback signal to the controller.

14. A hydraulic driver of a magnetic resonance elastography (MRE) system, wherein the hydraulic driver is adapted to be connected to at least a passive actuator for contacting with a subject, the hydraulic driver comprising:
    a pump;
    a hydraulic piston-cylinder unit operatively coupled to the pump; and
    a tube assembly comprising a proximal end in liquid communication with the hydraulic piston-cylinder unit and a distal end in liquid communication with the passive actuator;
    wherein the passive actuator oscillates in response to hydraulic energy generated in a liquid in the hydraulic driver as the pump drives the piston forward and backward in the cylinder of the hydraulic piston-cylinder unit; and
    wherein the tube assembly comprises a reservoir having at one end thereof an opening for liquid communication with a first tube extending from the piston-cylinder unit, and at an opposite end thereof an opening for liquid communication with a second tube leading to the passive actuator.

* * * * *